(12) United States Patent
Klomp et al.

(10) Patent No.: US 9,243,466 B2
(45) Date of Patent: Jan. 26, 2016

(54) DETERMINING METHANE CONTENT OF A BOTTOM SAMPLE

(75) Inventors: Ulfert Cornelis Klomp, Amsterdam (NL); Thomas Alexander Pasfield, Amsterdam (NL); Kjeld Aaby Sørensen, Rijswijk-Zh (NL)

(73) Assignee: Shell Oil Company, Houston, TX (US)

( * ) Notice: Subject to any disclaimer, the term of this patent is extended or adjusted under 35 U.S.C. 154(b) by 682 days.

(21) Appl. No.: 13/516,272

(22) PCT Filed: Nov. 15, 2010

(86) PCT No.: PCT/EP2010/067439
§ 371 (c)(1),
(2), (4) Date: Jun. 15, 2012

(87) PCT Pub. No.: WO2011/082870
PCT Pub. Date: Jul. 14, 2011

(65) Prior Publication Data
US 2012/0261191 A1    Oct. 18, 2012

(30) Foreign Application Priority Data

Dec. 17, 2009   (EP) ..................................... 09179586

(51) Int. Cl.
| | | |
|---|---|---|
| *E21B 25/18* | (2006.01) | |
| *E21B 49/02* | (2006.01) | |
| *E02F 5/00* | (2006.01) | |
| *E21B 25/00* | (2006.01) | |

(Continued)

(52) U.S. Cl.
CPC .................. *E21B 25/18* (2013.01); *E02F 5/006* (2013.01); *E21B 25/00* (2013.01); *E21B 43/01* (2013.01); *E21B 47/10* (2013.01); *E21B 49/025* (2013.01); *E21C 50/00* (2013.01); *E21B 2043/0115* (2013.01); *G01N 1/4022* (2013.01); *G01N 2001/2229* (2013.01)

(58) Field of Classification Search
CPC ....... E21B 49/00; E21B 49/001; E21B 49/02; E21B 49/025; E21B 25/18; E21B 25/00
See application file for complete search history.

(56) References Cited

U.S. PATENT DOCUMENTS 3,853,196 A * 12/1974 Guest ............................. 180/8.5
4,544,037 A * 10/1985 Terry ............................. 166/369

(Continued)

FOREIGN PATENT DOCUMENTS

WO    WO2009089528    7/2009 ............. E21B 15/02

OTHER PUBLICATIONS

Kolle, J.J., and M.D. Max. "Seafloor Drilling of the Hydrate Economic Zone for Exploration and Production of Methane." Tempress Technologies, Jun. 15, 2000. Web. Jan. 8, 2015. <http://ttinc10.qwestoffice.net/papers/hydratedrill.pdf>.*

(Continued)

*Primary Examiner* — Giovanna C Wright
*Assistant Examiner* — Tara Schimpf

(57) ABSTRACT

A methane content of a bottom sample comprising methane hydrate crystals is determined by:—taking a core sample (5) from a bottom sediment (3) in a deepwater area;—storing the core sample (5) in a storage chamber (4);—lifting the storage chamber (4) to a predetermined waterdepth (BGHZ=Base of Gas Hydrate stability Zone) at which any methane hydrate crystals in the core sample (5) dissociate into water and methane; and—measuring an amount of methane released by the lifted core sample (5).

9 Claims, 3 Drawing Sheets

(51) Int. Cl.
  *E21B 43/01*  (2006.01)
  *E21B 47/10*  (2012.01)
  *E21C 50/00*  (2006.01)
  *G01N 1/40*  (2006.01)
  *G01N 1/22*  (2006.01)

(56) References Cited

U.S. PATENT DOCUMENTS

| | | |
|---|---|---|
| 6,659,204 B2 | 12/2003 | Aumann et al. ............. 175/244 |
| 2002/0033281 A1 | 3/2002 | Aumann et al. ............. 175/244 |
| 2008/0162056 A1* | 7/2008 | Greaves ........................ 702/24 |
| 2009/0178848 A1* | 7/2009 | Nellessen, Jr. et al. ........... 175/7 |
| 2010/0161229 A1* | 6/2010 | Georgi et al. .................. 702/11 |
| 2011/0309668 A1* | 12/2011 | Efthymiou et al. ............. 299/17 |

OTHER PUBLICATIONS

Heeschen, K.U. et al "In Situ Hydrocarbon Concentrations from Pressurized Cores in Surface Sediments Northern Gulf of Mexico"; Marine chemistry; vol. 107, No. 4; pp. 498-515; Dec. 20, 2007.

Shijltheiss, P. et al.; "Wireline Coring and Analysis Under Pressure, Recent Use and Future Developments of the Hyacinth System"; Scientific Drilling Journal; pp. 44-50; Mar. 7, 2009.

Lorenson, T.D. et al; "4. Gas Content and Composition of Gas Hydrate from Sediments of the Southeastern North American Continental Margin"; Proceedings of the Ocean Drilling Program Scientific Results; vol. 164; pp. 37-46; Apr. 21, 1998.

* cited by examiner

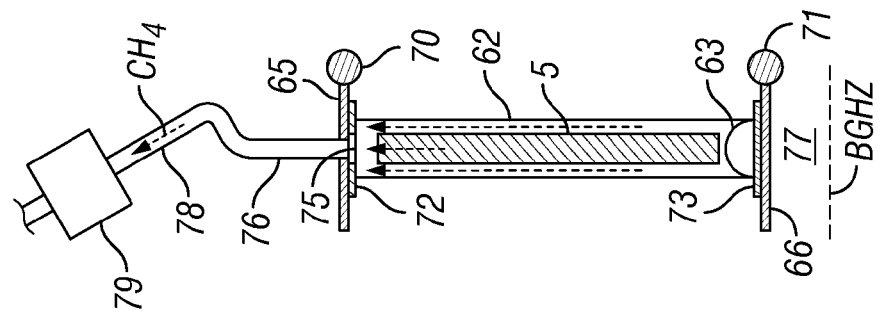
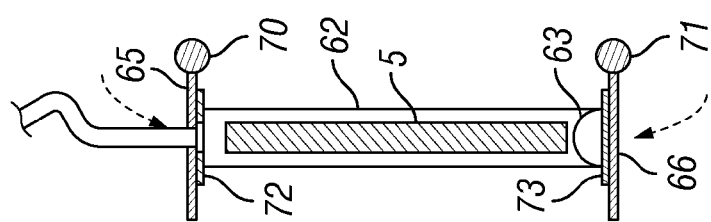
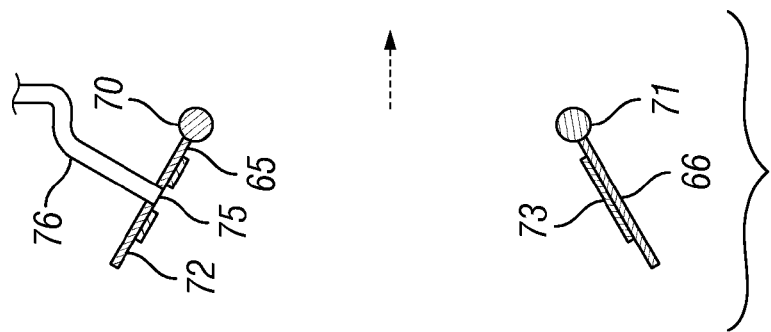
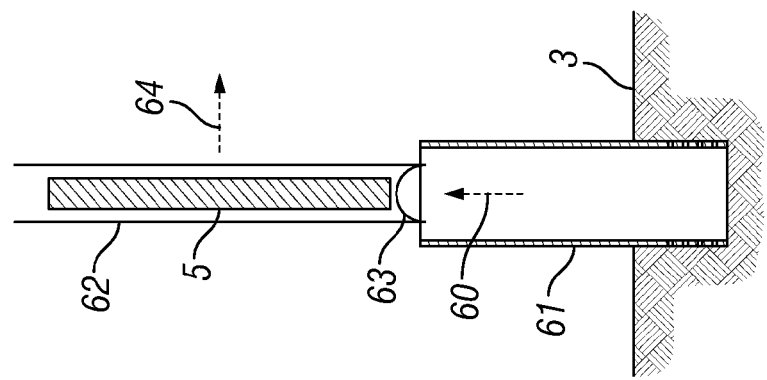

DETERMINING METHANE CONTENT OF A BOTTOM SAMPLE

PRIORITY CLAIM

The present application claims priority from PCT/EP2010/067439, filed 15 Nov. 2010, which claims priority from EP 09179586.4, filed 15 Dec. 2009.

BACKGROUND OF THE INVENTION

The invention relates to a method and system for determining a methane content of a bottom sample.

Such a method and system are known from U.S. Pat. No. 6,659,204 and from the papers:

"In situ hydrocarbon concentrations from pressurized cores in surface sediments, Northern Gulf of Mexico" published by K. U. Heeschen et al in the magazine Marine Chemistry, vol. 107, issue no. 4, pages 498-515, published on 20 Dec. 2007, (XP002569753); and "Wireline Coring and Analysis under Pressure, Recent Use and Future Developments of the Hyacinth System" published by P. Shultheiss et al in the Scientific Drilling Journal issued on 7 Mar. 2009, (XP002569762,ISSN: 1816-8957).

The core sampling methods and systems known from these prior art references comprise a core sampler for evaluating methane hydrate resources, in which core samples are stored at an in-situ pressure and temperature to inhibit decomposition of hydrate crystals due to pressure decrease and/or temperature increase when the core samples are lifted to surface.

A disadvantage of these known pressurized core samplers is that they are expensive and unreliable with a frequent failure to recover the sample at a lower than in-situ pressure and/or at a higher than in-situ temperature which may cause a systematic bias in the reported hydrate content from successful cores.

Accordingly direct measurement of core data as known from these prior art references is unreliable as hydrates may dissociate so that is not known how much hydrates may be lost after the core sample has been taken.

One of the key challenges in economically developing hydrate resources, which are often located in deepwater and/or arctic areas, lies in finding low-cost methods to find and evaluate shallow methane hydrate deposits.

One of the biggest challenges has been measuring the actual hydrate content of cores recovered during drilling offshore, as current techniques are both unreliable and expensive.

Problems with other currently available hydrate sampling and hydrate detection techniques are that:

Indirect geophysical methods (EM, Seismic) are unreliable due to the nature of hydrates.

Estimate of hydrate content based on water freshening is unreliable due to uncertaintly over baseline porewater salinity.

There is a need to provide an improved technique for measuring the methane content of hydrate-bearing cores which is expected to be both cheaper and more reliable than existing methods and systems.

SUMMARY OF THE INVENTION

In accordance with the invention there is provided a method for determining a methane content of a bottom sample, the method comprising:

taking a core sample from a sediment in a waterbottom;

storing the core sample in a storage chamber;

lifting the storage chamber and core sample to a predermined water depth at an ambient pressure at which any methane-hydrate crystals in the core sample dissociate into water and methane;

measuring an amount of methane released by the lifted core sample; and determining the methane content of the sediment on the basis of the amount of methane released by the lifted core sample.

If the bottom sediment is located in a deepwater area at which methane-hydrate crystals remain stable then the the storage chamber and core sample may be lifted from the waterbottom to a waterdepth at which the ambient pressure is lower than a methane-hydrate dissociation pressure of any methane-hydrate crystals in the core sample, thereby inducing any methane-hydrates in the lifted sample to dissociate into methane and water. The amount of methane released by the core sample may be measured by a methane sensing device which is connected by a conduit to the storage chamber which is located on a vessel floating at the water surface.

If the bottom samples identify a recoverable amount of methane hydrates in the bottom sediment the methane hydrates may be subsequently excavated from the bottom sediment, whereupon the excavated methane hydrates are depressurized and/or heated to induce the methane-hydrates to dissociate and release methane which is subsequently exported to market or converted into a marketable product, such as pipelineable natural gas for industrial or domestic use, Liquid Natural Gas (LNG) and/or synthetic Gas To Liquid (GTL) products.

In accordance with the invention there is further provided a system for determining a methane content of a bottom sample, the system comprising:

a core sampling device for taking a core sample from a sediment in a water bottom;

a storage chamber for storing the core sample;

means for lifting the storage chamber and core sample to a predetermined waterdepth at an ambient pressure at which any methane-hydrate crystals in the core sample dissociate into water and methane;

a methane sensing device for measuring an amount of methane released by the lifted core sample; and means for determining the methane content of the bottom sediment on the basis of the amount of methane released by the lifted core sample.

The core sampling device may comprise:

a frame which is mounted on legs, wheels and/or caterpillar mechanism, that is configured to move the frame in any desired direction across the bottom of a body of water; and a vertical core drilling device which is configured to move each core sample into a core sample storage chamber that is configured to store the core sample at a pressure which is substantially equal to the ambient pressure of a fluid, such as seawater, surrounding the device and that forms part of bundle of core sample storage chambers which is mounted as a rotatable and removable carousel assembly on the frame and which is connected to a bundle of flexible conduits that are secured to a hoisting line that is suspended from a floating vessel.

These and other features, embodiments and advantages of the method and system according to the invention are described in the accompanying claims, abstract and the following detailed description of non-limiting embodiments depicted in the accompanying drawings, in which description reference numerals are used which refer to corresponding reference numerals that are depicted in the drawings.

BRIEF DESCRIPTION OF THE DRAWINGS

FIG. 6 shows an alternative configuration of a sealable core sampling chamber;

FIG. 7 shows how the upper and lower jaws of a carousel assembly are pivoted to seal the core sampling chamber of FIG. 6;

FIG. 8 shows the core sampling chamber of FIG. 6 sealed by the upper and lower jaws; and FIG. 9 shows how methane gas ($CH_4$) is released by hydrate dissociation in the depressurized core sample after lifting the core sample chamber to a waterdepth above the BGHZ (Base of Gas Hydrate stability Zone).

DETAILED DESCRIPTION OF THE DEPICTED EMBODIMENTS

Figure 1:
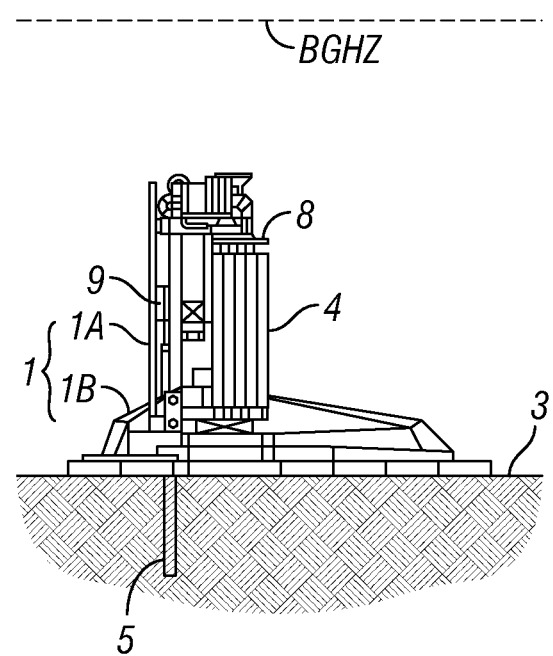
FIG. 1 shows an underwater core sampling device which carries a bundle of core sampling chambers.

The method and system according to the invention provide a novel technique for evaluating the total methane content of a core sample containing methane hydrate and recovered from the seabed at a water depth within the Base of Gas Hydrate stability Zone (BGHZ). Historically this has been difficult as the normal technique applied is to recover core samples to a surface vessel for analysis. During the journey up to the sea surface the core leaves the gas hydrate stability zone (in water depths shallower than about 400 m depending on temperature) and the methane hydrate within the core starts to dissociate. By the time the core has reached the vessel (typically limited by the speed at which the coring device can be winched to the vessel) an unknown amount of dissociation will have occurred and the evolved gas will have escaped, such that the initial amount of hydrate prior to dissociation cannot be known. Techniques exist for estimating the amount of gas evolved, such as measuring residual water salinity and calculating the freshening which has occurred relative to a background initial level, but since the initial salinity can only be guessed at it is hard to have confidence in hydrate content estimates obtained in this fashion.

To overcome this, the technique of 'Pressure Coring' as disclosed in U.S. Pat. No. 6,659,204, has been used to seal the core samples in an airtight container at the point of sampling, such that as the core is recovered to the surface vessel the pressure within the container does not drop with reducing ambient water pressure. The pressure core, once recovered to the vessel, can be analyzed using x-ray or CAT scanners to visualize hydrate deposits, and the amount of gas present can be measured by reducing the internal pressure in a controlled manner which capturing and measuring the volume of gas released.

Problems with pressure coring technique known from U.S. Pat. No. 6,659,204 are as follows:

High cost: these are expensive core receptacles.

Difficult handling: they require quite specialized handling facilities within the drilling equipment used to obtain a good sample.

Low reliability: they frequently fail to recover the core sample at pressure. This is often due to the failure to obtain an airtight seal in the ball valve which allows the core to enter the core receptacle.

Low reliability is particularly problematic as the failure to get an airtight seal may be related to the nature of the material being cored. Sandy samples may be more likely to have a poor seal, and sandy samples are often the most hydrate-rich. Therefore the pressure core system may have an inbuilt bias in that it preferentially recovers samples with low hydrate contents.

The method and system according to the present invention do not aim to recover the samples to the surface vessel with the hydrate intact. In contrast, the aim is to allow hydrate within the core sample to dissociate fully while the core is still at some depth within the water column. As the hydrate dissociates however, all of the evolved gas is collected and/or measured such that the total volume of methane evolved from the core is known, and therefore the initial methane content of the core is known. From this information, and knowledge about the solubility of methane within water at depth, the hydrate content of the core can be reliably calculated.

FIG. 1 shows a core sampling device 1 according to the invention, which device 1 comprises a frame 1A mounted on movable legs 1B that allow the device 1 to move in any direction across the waterbottom 3. The frame 1A carries a bundle of core sampling chambers 4 consisting of a number of tubes which are each large enough to easily contain one core sample 5 taken from the waterbottom 3. The tubes may be PVC tubes that typically have a diameter of about 10 cm and a length of between 1 and 2 m.

FIG. 1 shows that the core sampling chambers 4 are secured as a bundle to a carousel assembly 8, which is rotatably mounted on the frame 1A.

FIG. 1 further shows that the frame 1A carries a conventional seabed-drilling device 9, such as a Benthic Geotech PROD drilling device as known from International patent application WO2009/089528, which collects a number of hydrate-containing core samples 5 from the waterbottom 3 and inserts the collected samples into the core sampling chambers 4, which are supported by the rotatable carousel assembly 8.

While the core sampling device 1 remains on the waterbottom 3, the bundle of gas collecting chambers 4 filled with the core samples 5 is removed from the carousel assembly 8. This sort of manipulation task should not be difficult using for example a work-class ROV (Remotely Operated Vehicle). It may be possible to integrate the open-bottomed core sampling chambers 4 with the carousel assembly 8 such that this transfer step is avoided altogether.

Figure 2:
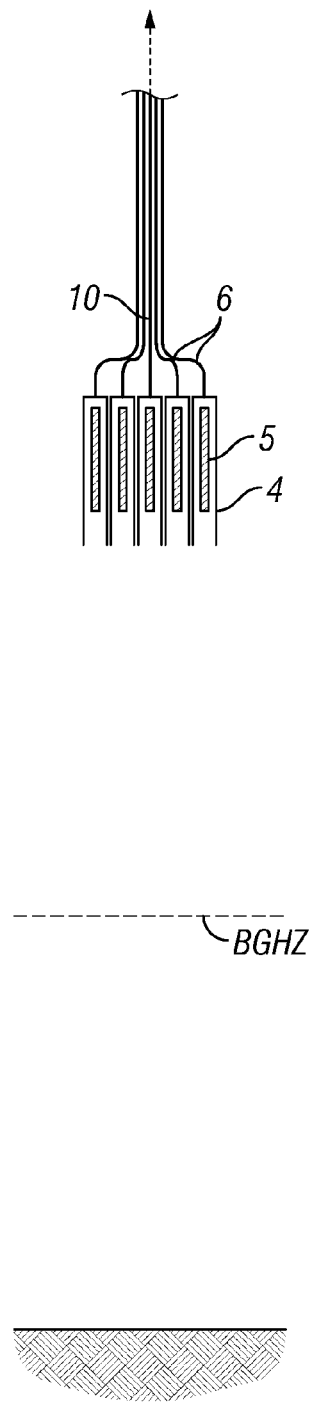
FIG. 2 shows how a bundle of core sampling chambers filled with core samples after removal from the underwater core sampling device.
Figure 3:
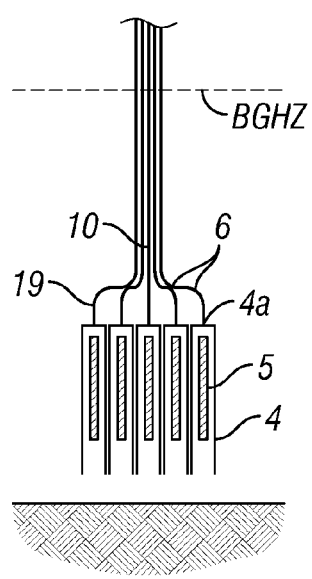
FIG. 3 shows how the bundle of core sampling chambers is lifted to a waterdepth above the Base of Gas Hydrate stability Zone(BGHZ)
Figure 4:
FIG. 4 shows how the bundle of core sampling chambers containing the methane and hydrate depleted core samples may subsequently be lifted to a ship or other floating vessel for further analysis in an offshore or onshore laboratory.

As shown in more detail in FIGS. 2-4 the core sampling chambers 4 are tubes which are open at the bottom and closed at the top and that the closed top 4A of each tube comprises a hole 19 leading to a flexible gas-tight conduit 6, which is at its upper end connected to a methane sensing assembly at a floating vessel (not shown).

FIGS. 2 and 3 show that, after removal from the core sampling device 1, the bundle of core sampling chambers 4 is lifted, such as by a hoisting cable 10 connected to a winch on a floating vessel (not shown), to a waterdepth above the Base of the Gas Hydrate stability Zone (BGHZ), such as a water depth of between 100 m and 400 m, with each core sampling chamber 4 comprising a single core sample 5. under these changed ambient conditions the hydrate in the core samples 5 will start to dissociate, evolving methane($ch_4$) gas 11 and fresh water. the released methane$_{(CH4)}$ gas 11 will rise within the core sampling chamber 4 under buoyancy and escape via the hole 19 into the flexible conduit 6. Having escaped the chamber 4, the methane($CH.sub.4$) will rise buoyantly within conduit 6 and float, as indicated by the arrow in FIG. 3, to the methane sensing device(not shown) at the for measurement and analysis.

FIG. 4 shows that after all the hydrate has dissociated from the core samples 9 (which will likely be evident from the cessation of methane collecting in the top of the open-bottomed chambers 4) the bundle of gas collecting chambers 4 may be recovered to the surface vessel, where the core samples can be removed from the chambers 4 and the remaining sediment and water within the chambers 4 can be retrieved for later analysis.

Figure 5:
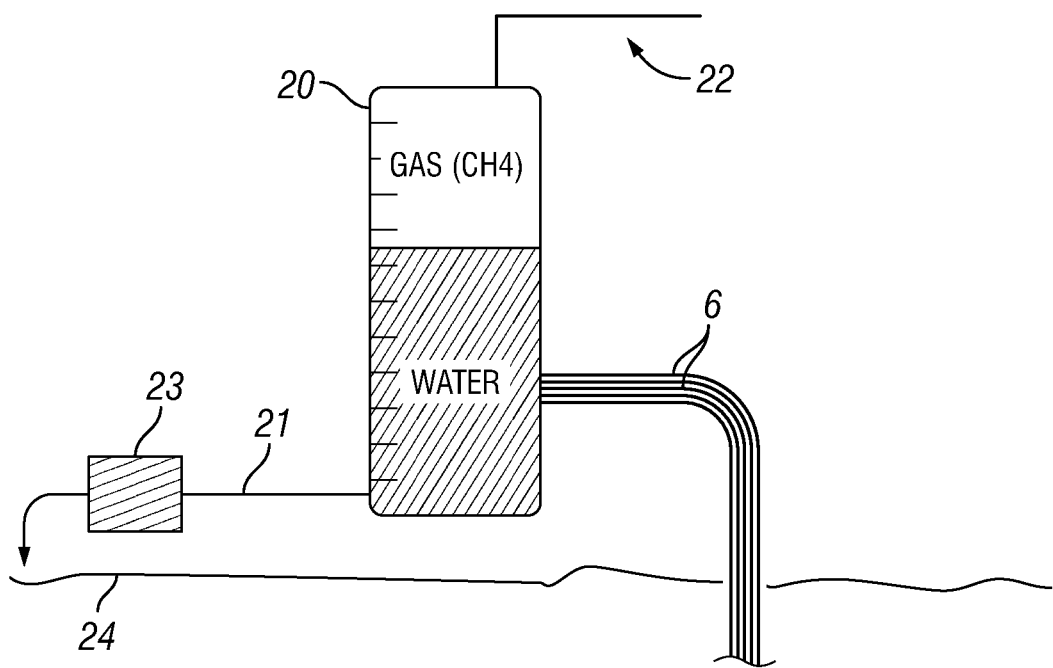
FIG. 5 shows a gas water separation tank mounted on a ship or other floating vessel from which the collected methane is discharged to a gas metering and analysis device.

If the method and system according to the invention identify recoverable hydrate deposits in the waterbottom then a production system may be installed at the site from which the core samples have been taken, which production system may excavate a slurry of methane hydrate, sediment and seawater from the waterbottom and which pumps the excavated slurry up through a riser to a production platform at the water surface, where methane may be separated from the slurry and exported to market. FIG. 5 shows the optional surface vessel topsides equipment comprising a water-gas separation tank 20, which is connected to the upper ends of the conduits 6 shown in FIG. 3, and also to a water discharge conduit 21 and to a gas discharge conduit 22.

The water discharge conduit 21 comprises a water pump 23 which pumps the collected water into a water disposal tank or, after optional cleaning, into the body of water 24.

A separate water-separation tank 20 may be connected to each of the flexible gas/water conduits 6, and therefore to each of the open-bottomed steel sample storage chambers 4. In such case each conduit 6 enters a separate gas-liquid separation tank 20 which is initially filled with water. This tank 20 may have graduated glass side windows or some other means of readily identifying the level of water within the tank 20. To the bottom of the tank 20 is connected a water pump 23 which gradually draws seawater from the storage tank, causing water to be drawn in from the sample storage chamber 4 via the flexible gas/water conduit 6. The water passing through the water pump 23 may be cleaned and then discharged into the sea or stored for later analysis (e.g. of salinity for evidence of freshening due to hydrate dissociation).

As the hydrate dissociates and gas enters the top of the open-bottomed sample storage chamber 4, a mixture of gas and water passes up the flexible water/gas conduit 6 and enters the water-gas separation tank 20. Upon entering the tank 20 the gaseous portion of the mixture rises to the top of the tank 20 and the water portion mixes with the water already in the storage tank 20. Thus all the methane gas ($CH_4$) evolved from the core sample chamber 4 is collected in the storage tank 20. The volume of gas can easily be measured, and it can be drawn from the top of the storage tank 20 for separate storage and/or analysis (e.g. of composition).

The method according to the invention may be applied in a number of alternative embodiments, such as:

A) Eliminating the flexible conduits 6 to retrieve the gas to the surface vessel during dissociation, but instead simply making the open-bottomed sample collecting chambers 4 sufficiently large to store all of the evolved gas. The quantity of gas in the open-bottomed sample collecting chambers 4 can be reliably estimated by observing the water level in the open-bottomed tube prior to recovery, for example using an acoustic device such as an echosounder within the open-bottomed tube to estimate the height of the gas-containing portion.

B) Allowing the gas to escape from the top of the open-bottomed sample collecting chambers 4 via a metering device which meters the volume and composition of the gas released through an orifice in the top of the sample collecting chamber 4. The metering device could be connected via a live data transfer cable to the vessel, or it could be equipped with a wireless measuring data transmission system or with recording device attached for retrieval of data at a later time. In the latter case, the recording device would need to record metered volume against pressure, since the volume of a given quantity of gas is pressure-dependent. A time-signature for the metered quantity may also serve this purpose, since under normal survey circumstances the depth below water of the survey equipment is time-logged, and therefore a conversion from time to water depth and therefore pressure is possible.

C) In case the manipulation of the filled core tubes underwater proves difficult, it may be possible to use a system of air-tight seals to make the core tube gastight as it is removed from the drill string. After raising the drilling rig to above the BGHZ, the gas hydrate will start to dissociate and the gas being driven off could be collected via gas lines (sent to the vessel or stored on the drill-rig) or metered as described above.

Although the gas tightness of the seals would not need to be rated to the same high pressure as required for preservation of gas hydrate, as achieved in the pressure coring technique known from U.S. Pat. No. 6,659,204 it is possible to store and depressurize the core sample in a substantially sealed sample storage chamber.

FIGS. 6-9 show how a core sample may be stored and depressurized in a substantially sealed sample storage chamber.

In FIG. 6 arrow 60 shows how a core sample 5 is raised out of the drillpipe 61 of the core sampling device 1 (as shown in FIG. 1) and then inserted into steel core sample holding tube 62, which is equipped at its lower end with a core catcher 63.

In FIG. 7 arrow 64 shows how the core sample holding tube 62 is moved into pivotal jaws 65, 66 of pressure sealing equipment of the carousel assembly 8(as shown in FIG. 1).

FIG. 8 shows how the jaws 65,66 are pivoted about pivots 70,71 such that elastomeric seals 72,73 are pressed against the upper and lower ends of the core sample holding tube 62. The upper jaw 65 comprises an opening 75 which is connected to a flexible gas release conduit 76.

FIG. 9 shows how the core sample 5 is depressurized by lifting the sealed core sample tube 62 to a waterdepth lower than the BHGZ, wherein the depressurization is effectuated by the flexible wall of the gas release conduit 76, which acts as a pressure equalization membrane between the exterior and interior of the conduit 76 so that the fluid pressure in the pores of the core sample 5 is substantially equal to the ambient pressure of the surrounding seawater 77, which pressure is at the waterdepth lower than the BHGZ such that any methane hydrates in the core sample 7 dissociate into water and methane($CH_4$)and any methane will rise through and alongside the core sample 5 and flow into the conduit 76 as indicated by arrows 78. the flux of methane 78 released by the core sample 5 may be metered by a methane flux meter 79 mounted adjacent to the opening 75 in the upper jaw 65. the released flux of methane 78 may be released into the seawater 77 or stored in a gas storage tank shown in FIG. 5 for further analysis. it will be understood that an advantage of the sealed core sample holding tube assembly shown in FIGS. 6-9 over the core sample tubes 4 with open bottoms shown in FIGS. 2-4 is that the core samples 5 will remain better intact for further analysis in a core sample investigation laboratory since no disintegrated parts of bottom sediment in the core samples 5 will fall from the open bottoms of the core sample holding chambers formed by the sealed core holding tubes 62 shown in FIGS. 6-9.

In summary the method and system according to the invention provide means whereby the methane content of a core sample is estimated by measurement of the volume of gas evolved by a gas-hydrate-containing core sample as it is lifted in the water column from the sampling depth to a level above the Base of the Gas Hydrate stability Zone (BGHZ).

The core sample storage chambers used in the system according to the invention preferably comprise open-bottomed tubes to contain the core samples and the gas evolved from the core samples.

The thus evolved gas may be lifted from the open-bottomed tube to a surface vessel where the volume of evolved gas evolved is measured.

Alternatively the evolved gas may be allowed to escape from the top of the open-bottomed tube via a gas metering system, thereby measuring the volume of gas evolved.

Alternatively of the gas evolved may be captured in the top of the open-bottomed tube and the height of the gas column may be measured, thereby measuring the volume of gas evolved.

The gas-collecting device may be an integral part of the seabed drilling and coring device, thereby avoiding the need for a transfer of cores from the core magazine to the gas-collecting device, wherein a gas-tight seal is created around the core tube within the storage carousel of the seabed drilling rig, thereby avoiding the need for the transfer of cores into an open-bottomed tube within the carousel.

It will be understood that the method according to the invention may be applied in any deepwater area in any body of water, such as an ocean, sea, fjord, lake or river and that references to deepsea and/or seabed should be read to apply to any body of water and/or the bottom of any body of water.

In summary, the methane content of an underwater methane-hydrate containing bottom sediment (3) may be determined in accordance with the present invention by:
taking a core sample (5) from the bottom sediment (3);
storing the core sample (5) in a storage chamber (4);
lifting the storage chamber (4) to a predetermined waterdepth(known as BGHZ=Base of Gas Hydrate stability Zone) at which methane hydrate crystals in the core sample (5) dissociate into water and methane; and
measuring an amount of methane released by lifted core sample(5).

What is claimed is:

1. A method for determining a methane hydrate content of a sample from a waterbottom, the method comprising:
taking a core sample from a sediment in a waterbottom;
storing the core sample in a storage chamber the storage chamber having an open bottom and a sealed top, the sealed top penetrated by a conduit so that methane released from the sample will percolate via the conduit into a methane sensing device wherein the methane sensing device located on a vessel floating at the water surface;
lifting the storage chamber and core sample to a predermined water depth at an ambient pressure at which any methane-hydrate crystals in the core sample dissociate into water and methane with the open bottom of the sample storage chamber remaining open;
measuring an amount of methane released by the lifted core sample via the methane sensing device;
recovering to the vessel the core sample wherein the core sample is recovered after methane hydrate has fully dissociated from within the core sample; and
determining the methane hydrate content of the bottom sediment on the basis of the amount of methane released by the lifted core sample.

2. The method of claim 1, wherein the bottom sediment is located in a deepwater area at which methane-hydrate crystals remain stable and the storage chamber is lifted from the waterbottom to a waterdepth at which the ambient pressure is lower than a methane-hydrate dissociation pressure of any methane-hydrate crystals in the core sample, thereby inducing any methane-hydrates in the lifted core sample to dissociate into methane and water.

3. The method of claim 1, wherein the core sample is taken by an underwater core drilling machine.

4. The method of claim 3, wherein the underwater core drilling machine is able to move itself across a water bottom.

5. The method of claim 3, wherein the underwater core machine comprises a frame mounted on legs, wheels and/or caterpillar mechanism, a vertical core drilling device which is configured to move each core sample into a core sample storage chamber that forms part of a bundle of core sample storage chambers the bundle of core sample storage chambers mounted as a rotatable and removable carousel assembly on the frame.

6. The method of claim 5, wherein the bundle of core sample storage chambers is connected to a bundle of flexible conduits that are secured to a hoisting line that is suspended from the floating vessel.

7. The method of claim 6, wherein the waterdepth is more than 400 meters and the bundle of core sample chambers is lifted by the hoisting line to a waterdepth above a hydrate stability zone at which the ambient water pressure is lower than the methane-hydrate dissociation pressure of any methane-hydrate crystals in the core sample, which zone is located at less than 400 meters water depth.

8. The method of claim 1, wherein if the bottom sample identifies a recoverable amount of methane hydrates in the bottom sediment the methane hydrates are subsequently excavated from the bottom sediment, whereupon the excavated methane hydrates are depressurized and/or heated to induce the methane-hydrates to dissociate and release methane.

9. The method of claim 8, wherein the produced methane is converted into a marketable product, selected from the group consisting of pipelineable natural gas, Liquid Natural Gas (LNG) and Gas To Liquid (GTL) products.

* * * * *